(12) United States Patent
Surh et al.

(10) Patent No.: US 7,118,661 B2
(45) Date of Patent: Oct. 10, 2006

(54) NANOLAMINATE MICROFLUIDIC DEVICE FOR MOBILITY SELECTION OF PARTICLES

(75) Inventors: Michael P. Surh, Livermore, CA (US); William D. Wilson, Pleasanton, CA (US); Troy W. Barbee, Jr., Palo Alto, CA (US); Stephen M. Lane, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 394 days.

(21) Appl. No.: 10/261,392

(22) Filed: Sep. 30, 2002

(65) Prior Publication Data
US 2004/0060822 A1 Apr. 1, 2004

(51) Int. Cl.
*G01N 27/453* (2006.01)
(52) U.S. Cl. .................. 204/601; 204/643; 422/100
(58) Field of Classification Search ............... 204/450, 204/601, 547, 643; 422/100
See application file for complete search history.

(56) References Cited

U.S. PATENT DOCUMENTS

| 4,900,414 A | * | 2/1990 | Sibalis | 204/457 |
| 5,818,055 A | * | 10/1998 | Franzen | 250/292 |
| 6,596,143 B1 | * | 7/2003 | Wang et al. | 204/547 |
| 2003/0129087 A1 | * | 7/2003 | Barbee et al. | 422/58 |
| 2004/0011652 A1 | * | 1/2004 | Bressler | 204/643 |

* cited by examiner

*Primary Examiner*—Kaj K. Olsen
(74) *Attorney, Agent, or Firm*—John P. Wooldridge; L. E. Carnahan; Alan H. Thompson

(57) ABSTRACT

A microfluidic device made from nanolaminate materials that are capable of electrophoretic selection of particles on the basis of their mobility. Nanolaminate materials are generally alternating layers of two materials (one conducting, one insulating) that are made by sputter coating a flat substrate with a large number of layers. Specific subsets of the conducting layers are coupled together to form a single, extended electrode, interleaved with other similar electrodes. Thereby, the subsets of conducting layers may be dynamically charged to create time-dependent potential fields that can trap or transport charge colloidal particles. The addition of time-dependence is applicable to all geometries of nanolaminate electrophoretic and electrochemical designs from sinusoidal to nearly step-like.

2 Claims, 2 Drawing Sheets

NANOLAMINATE MICROFLUIDIC DEVICE FOR MOBILITY SELECTION OF PARTICLES

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to nanolaminated microfluidic devices, particularly to multiple-interleaved nanolaminate device for steady-state electrophoretic transport within a fluid channel, and more particularly to nanolaminate microfluidic devices using time dependent voltage envelopes to enable the simultaneous travel of different voltage envelopes in different directions, at different speeds, and provides time-dependent voltage profiles which encompass all conceivable time dependences, from sinusoidal to nearly step-like, and permits discrimination or separation of particles based on their dynamics or mobilities.

Electrophoretic and electrochemical devices have been proposed that employ flat, polished, exposed surfaces of nanolammate composites to enhance the detection of dilute analyte particles. The nanolaminate composites were formed by magnetron sputtering of alternating layers of a conductive material and an insulative material, such as silica and alumina, whereafter the composites were cut and polished to expose a nanolaminate surface as a sensor. These prior nanolaminate composites or structures are exemplified by the sensor template described and claimed in copending U.S. Patent Application Publication Number 2003-0129087, filed Jun. 11, 2002.

The present invention involves a multiple-interleaved nanolaminate microfluidic device for steady-state electrophoretic transport within a fluid channel. The present invention utilizes slow time-dependent effects which offer improvements in the multiple-interleaved nanolaminate devices. Under the present invention, specific subsets of the conductive or metallic layers of the nanolaminate are coupled together to form a single, extended electrode, interleaved with other similar electrodes. Thereby, the subsets of metallic layers may be dynamically charged to create time-dependent potential fields that can trap or transport charge colloidal particles.

SUMMARY OF THE INVENTION

It is an object of the present invention to provide a nanolaminate microfluidic device for mobility selection of particles.

A further object of the invention is to provide time-dependent voltage profiles for nanolaminate microfluidic devices.

Another object of the invention is to provide nanolaminate microfluidic devices with time-dependent voltage profiles which permits discrimination or separation of particles based on their dynamics or mobilities.

Another object of the invention is to provide specific subsets of the conductive layers of a nanolaminate structure which may be coupled together to form a single, extended electrode, interleaved with other similar electrodes.

Another object of the invention is to provide nanolaminate structures with subsets of conductive layers which may be dynamically charged to create time-dependent potential fields that can trap or transport charge colloidal particles.

Other objects and advantages of the present invention will become apparent from the following description and accompanying drawings. The invention is directed to nanolaminate microfluidic devices for mobility selection of particles. The invention involves a multiple-interleaved nanolaminate structure for electrophoretic transport within a fluid channel which involves slow time-dependent effects. Specific subsets or voltage envelopes of the conductive (metallic) layers of the nanolaminate are coupled together to form a single, extended electrode, interleaved with other similar electrodes. The voltage envelope can be generalized to encompass a smooth distribution over several adjacent layers. Also, superposition of the voltage profiles would permit the simultaneous travel of different voltage envelopes in different directions, at different speeds, etc. The time-dependent voltage profiles encompass all conceivable time dependences, from sinusoidal to nearly step-like. The invention permits discrimination or separation of particles based on their dynamics or mobilities.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

Figure 1:
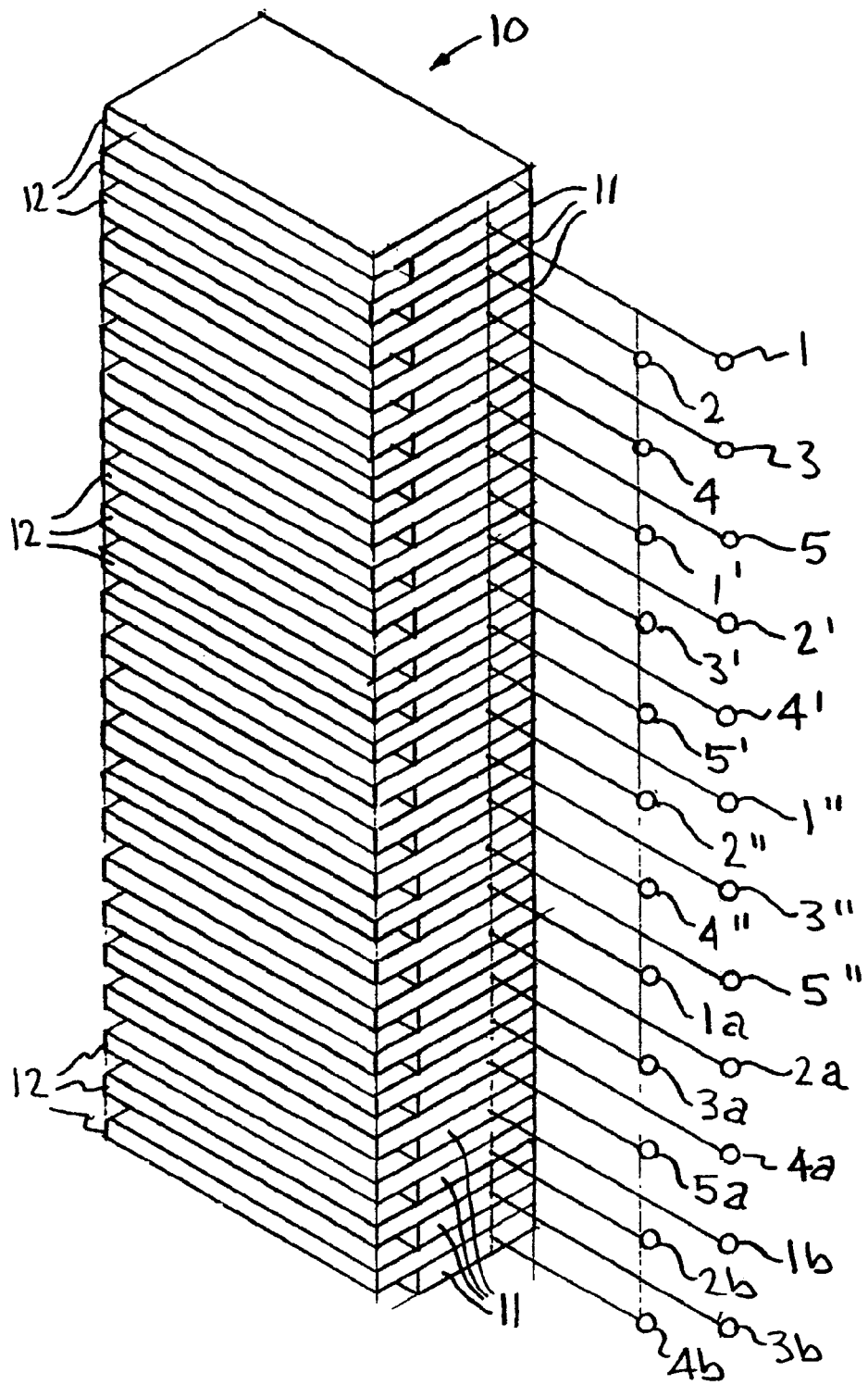
FIG. 1 is a view of a nanolaminate structure with electrodes extending from the conductive (metallic) layers of the structure.

The present invention is directed to nanolaminate microfluidic devices for mobility selection of particles. The invention involves a multiple-interleaved nanolaminate device that is capable of electrophoretic selection of particles on the basis of their mobility. Nanolaminate materials or structures contain a large number of (i.e., multiple) alternating layers of two or more, generally two, layers of different materials, generally conducting (metallic) and insulating. By this invention, specific subsets of the metallic layers are coupled together to form a single, extended electrode, interleaved with other similar electrodes. Thereby, the subsets of metallic layers may be dynamically charged to create time-dependent potential fields that can trap or transport charge colloidal particles.

This microfluidic component can be incorporated in a microfluidic device for the purpose of analyzing or performing a chemical or biological assay on very small fluid samples. Such devices can be used as pathogen detectors.

The present invention involves a component of a multiple-interleaved nanolaminate device for steady-state electrophoretic transport within a fluid channel. The invention incorporates into the nanolaminate device slow time-dependent effects which provide improvements to the device. The time-dependent features are provided by specific subsets of the metallic layers coupled together to form a single, extended electrode, interleaved with other electrodes.

By way of example, every first, sixth, eleventh, etc. metallic layer (labeled layer 1, 1', 1", 1a, 1b in FIG. 1) is given a particular voltage, V, while layers 2–5, 2'–5', etc. are kept at zero potential. All layers labeled 1 (1, 1', 1", 1a, and 1b in FIG. 1) are kept at the same voltage V, etc., (see FIG. 2). The periodicity may be defined as any number (N) greater than two. In the example here, N=5. The electrodes are assumed to be constructed such that the pattern then repeats every five, ten, $N^{th}$ metal layers along the channel. Now, the voltage at layers 1 is slowly returned to zero, and simultaneously the voltage of layers 2 (2, 2', 2", 2a and 2b in FIG. 1) is brought up to the value of voltage V, as above (See FIG. 3). Once the process is completed, the original voltage distribution (envelope) peaked at 1 has been displaced to 2. This process, can be repeated between layers 2 and 3, then 3 and 4, then 4 and 5, then 5 and 1' at a specified effective velocity. If the velocity is matched to the diffusivity of some charged particle, it may be possible to efficiently transport it, while leaving slower diffusers largely undisturbed. Driving down the array of metallic layers at some particular speed can be alternated with driving up the array at some higher speed so as to select from particles within a particular mobility window while leaving behind faster and slower diffusers.

The subset of metal layers 1, 1', 1", 1a, 1b, etc. are kept at the same voltage by interconnecting them. Similarly, layers 2, 2', 2", 2a, 2b, etc. are interconnected, etc. The subsets include conductive layers selected from each $N^{th}$ layer, where $N^{th}$ is defined as a number greater than two. For example, if N=5, the $1^{st}$, $6^{th}$, $11^{th}$, $16^{th}$, etc. layers are connected together to make a single electrode. Similarly the $2^{nd}$, $7^{th}$, $12^{th}$, $17^{th}$, etc. layers are connected to make a second electrode, similarly the $3^{rd}$, $8^{th}$, $13^{th}$, $18^{th}$, etc. layers are connected to a third electrode. The $4^{th}$, $9^{th}$, $14^{th}$, $19^{th}$, etc. layers are connected to fourth electrode, and the $5^{th}$, $10^{th}$, $15^{th}$, $20^{th}$, etc. layers are connected making 5 interdigitated electrodes in all.

Referring now to the drawings, FIG. 1 illustrates a nanolammate structure or stack 10 of alternating layers of conductive metallic material 11 and insulating material 12. Note that the front edges of metallic layers 11 have been etched back relative to the insulating layers 12, such as by the method described and claimed in U.S. Pat. No. 6,818,964, entitled "Selective-Etched Nanochannel Electrophoretic and Electrochemical Devices", assigned to the same assignee. This feature is not required for the operation of the device. Each of metallic layers 11 have a conductor or wire attached thereto and which are numbered in subsets of 1–5; namely, 1–5, 1'–5', 1"–5", 1a–5a, and 1b–4b, there being a total of 24 metallic layers 11 shown, but the structure or stack may include any number of alternating layers up to the limits of manufacturability.

Figure 2:
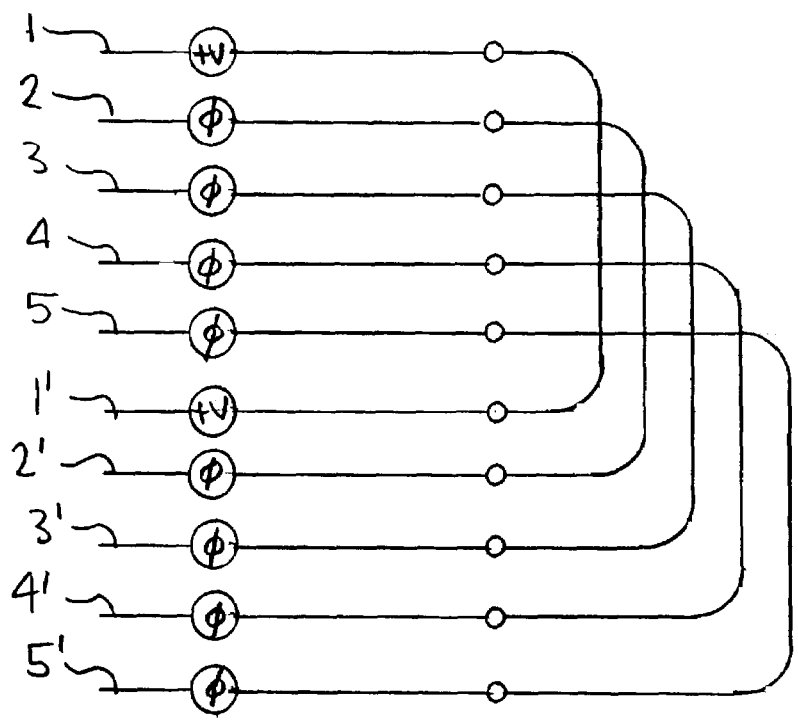
FIG. 2 schematically illustrates an embodiment of subsets of the metallic layers of the FIG. 1 structure to create time-dependent potential fields, shown at a specific time.
Figure 3:
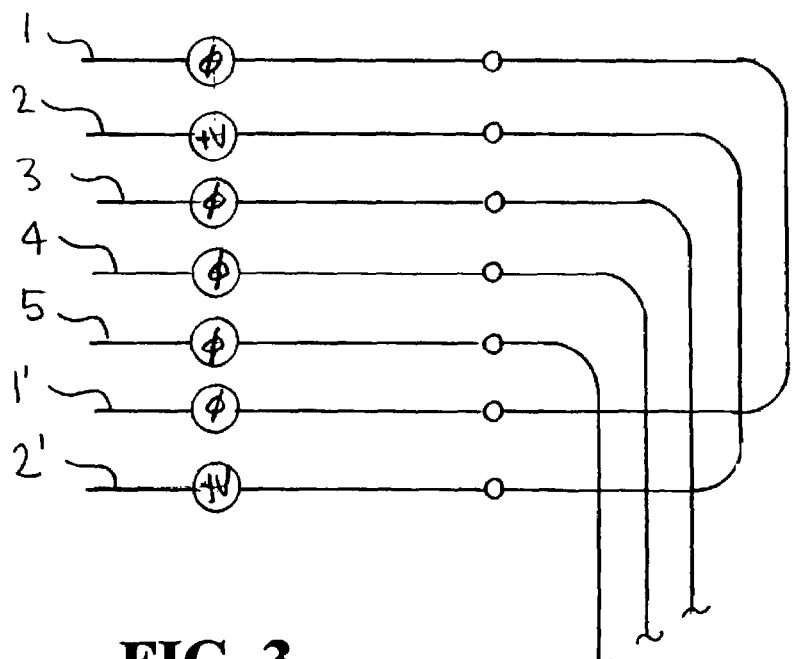
FIG. 3 schematically illustrates an embodiment of the same subset of the metallic layers of the FIG. 1 structure, at a subsequent time.

FIG. 2 illustrates the application of a voltage V to the layers labeled 1, 1', etc. as described above, while FIG. 3 schematically illustrates the voltage at layers 1 having been returned to zero and simultaneously the voltage of layers 2 is brought up to V, as described above.

The voltage envelope, described above, can be generalized to encompass a smooth distribution over several adjacent layers of the conductive material of the nanolaminate. The effective movement of the envelope with time then becomes more gradual in nature, and the rate of charging that is required to move the envelope at some particular speed is reduced. Also, superposition of the voltage profiles would permit the simultaneous travel of different voltage envelopes in different directions, at different speeds, etc. The time-dependent voltage profiles encompass all conceivable time dependences, from sinusoidal to nearly step-like. The additional improvement of time-dependence provided by this invention is applicable to all geometries of nanolaminate electrophoretic and electrochemical designs. The invention permits discrimination or separation of particles based on their dynamics or mobilities.

It has thus been shown that the present invention provides microfluidic devices made from nanolaminate materials with the capability of electrophoretic selection of particles on the basis of their charge and mobility. This is accomplished by specific subsets of the metallic layers of the nanolaminate being coupled together to form a single, extended electrode, interleaved with other similar electrodes. The subsets of metallic layers may be dynamically charged to create time-dependent potential fields that can trap or transport charge colloidal particles. The time-dependent voltage profiles encompass all conceivable time dependences, from sinusoidal to nearly step-like.

While particular embodiments have been described and illustrated to exemplify and teach the principles of the invention, such is not intended to be limiting. Modifications and changes may become apparent to those skilled in the art, and it is intended that the scope of the invention be limited only by the scope of the appended claims.

What is claimed is:

1. An apparatus, comprising:
   alternating layers of conducting nanolaminate material and nanolaminate insulating material, wherein a first subset of said conducting layers is coupled together to form a first extended electrode, wherein a second subset of conducting layers is coupled together to form a second extended electrode, wherein said first extended electrode and said second extended electrode are interleaved; and
   means for dynamically charging said first subset of said conducting layers and said second subset of conducting layers to create time-dependent potential fields that can trap or transport charged particles.

2. The apparatus of claim 1, further comprising at least a third subset of said conducting layers coupled together to form at least a third extended electrode, wherein said first extended electrode and said second extended electrode and said at least a third extended electrode are interleaved, wherein said means further comprise means for dynamically charging said at least a third subset of conducting layers to create said time-dependent potential fields that can trap or transport said charged particles.

* * * * *